US011789030B2

(12) United States Patent
Goldenberg (10) Patent No.: US 11,789,030 B2
(45) Date of Patent: Oct. 17, 2023

(54) USE OF A GLOBAL ASSAY OF COAGULATION AND FIBRINOLYSIS TO AIDE IN THROMBOEMBOLISM

(71) Applicant: THE JOHNS HOPKINS UNIVERSITY, Baltimore, MD (US)

(72) Inventor: Neil Goldenberg, St. Petersburg, FL (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 227 days.

(21) Appl. No.: 17/398,695

(22) Filed: Aug. 10, 2021

(65) Prior Publication Data

US 2021/0396771 A1    Dec. 23, 2021

Related U.S. Application Data

(62) Division of application No. 16/770,324, filed as application No. PCT/US2018/064233 on Dec. 6, 2018, now abandoned.

(60) Provisional application No. 62/595,910, filed on Dec. 7, 2017.

(51) Int. Cl.
*G01N 33/86* (2006.01)
*C12Q 1/56* (2006.01)

(52) U.S. Cl.
CPC ............... *G01N 33/86* (2013.01); *C12Q 1/56* (2013.01)

(58) Field of Classification Search
None
See application file for complete search history.

(56) References Cited

FOREIGN PATENT DOCUMENTS

| CA | 2623142 C | 4/2006 |
|---|---|---|
| EP | 1802766 A4 | 5/2008 |
| WO | 2006036744 A3 | 4/2006 |
| WO | 2011057143 A1 | 5/2011 |

OTHER PUBLICATIONS

Goldenberg, et al., "Multicenter randomized controlled trial on Duration of Therapy for Thrombosis in Children and Young Adults {the Kids-DOTT trial): pilot/feasibility phase findings", J Thromb Haemost, Sep. 2015 , vol. 13, No. 9 pp. 1597-1605.
Bernard, et al., "The institution-based prospective inception cohort study: design, implementation, and quality assurance in pediatric thrombosis and stroke research", Semin Thromb Hemost, Feb. 2013 , vol. 39, No. pp. 10-14.
Goldenberg, et al., "Elevated plasma factor VIII and D-dimer levels as predictors of poor outcomes of thrombosis in children", N Engl J Med, Sep. 9, 2004, vol. 35, No. 11, pp. 1081-1088.
Bombardier, et al., "Monitoring hypercoagulability and hypofibrinolysis following acute venous Thromboembolism in children: application of the CloFAL assay in a prospective inception cohort study" Thromb Res, Sep. 2012, vol. 130, No. 3, pp. 343-349.
Andrew, et al., "Maturation of the hemostatic system during childhood", Blood, Oct. 15, 1992, vol. 80, No. 8, pp. 1998-2005.
Antovic, et al., "Increased hemostasis potential persists in women with previous thromboembolism with or without APC resistance", J Thromb Haemost, Dec. 2003, vol. 1, No. 12, pp. 2531-2535.
Antovic, et al., "Thrombin activatable fibrinolysis inhibitor and hemostatic changes with type I diabetes mellitus with and without microvascular complications", Blood Coagul Fibrinolysis, Sep. 2003, vol. 14, No. 6, pp. 551-556.
Butenas, et al., "Normal" thrombin generation, Blood, Oct. 1, 1999, vol. 94, No. 7, pp. 2169-2178.
Colucci, et al., "Deficiency of thrombin activatable fibrinolysis inhibitor in cirrhosis is associated with increased plasma fibrinolysis", Hepatology, Jul. 2003. vol. 38, No. 1, pp. 230-237.
Cvirn, et al., "Effects of antithrombin and protein Con thrombin generation in newborn and adult plasma", Thromb Res, Feb. 15, 1999, vol. 93, No. 4, pp. 183-190.
Cvirn, et al., "Low tissue factor pathway inhibitor (TFPI) together with low antithrombin allows sufficient thromin generation in neonates", J Thromb Haemost, Feb. 2003, vol. 1, No. 2, pp. 263-268.
Faber, et al., "Thrombin generation in platelet-rich plasma as a tool for the detection of hypercoagulability in young stroke patients", Pathophysiol Haemost Thromb, 2003, vol. 33, No. 1, pp. 52-58.
Giansily-Blaizot, et al., "Thrombin generation measurement in factor VII-depleted plasmas compared to inherited factor VII-deficient plasmas", Pathophysiol Haemost Thromb, 2003, vol. 33, No. 1, pp. 36-42.
He, et al., "A simple and rapid laboratory method for determination of haemostasis potential in plasma. II. Modifications for use in routine laboratories and research work", Thromb Res, Sep. 1, 2001, vol. 103, No. 5, pp. 355-361.
He, et al., "A laboratory method for determination of overall haemostatic potential in plasma. I. Method design and preliminary results" Thromb Res, Oct. 15, 1999, vol. 96, No. 2, pp. 145-156.

(Continued)

*Primary Examiner* — Robert J Yamasaki
(74) *Attorney, Agent, or Firm* — MH2 TECHNOLOGY LAW GROUP, LLP (57) ABSTRACT

The present invention provides methods for identification of subjects with a rise in plasma coagulability post-diagnosis of thrombotic event (and consequent increased risk for recurrent thromboembolism) as well as for identification of subjects without thrombotic event who exhibit a rise in plasma coagulability for which prophylactic anticoagulation may be warranted for TE prevention, and other methods for identification of perioperative subjects who are at heightened risk for perioperative bleeding and/or for requiring blood transfusion, using the CloFAL assay, to aid in clinical decision making regarding anticoagulant and/or adjunctive clinical management designed to mitigate this heightened thromboembolic risk.

12 Claims, 3 Drawing Sheets

(56) References Cited

OTHER PUBLICATIONS

He, et al., "Hypercoagulation in surgical postmenopausal women having hormone replacement with overdose estradiol", Blood Coagul Fibrinolysis, Dec. 2001, vol. 12, No. 8, pp. 677-681.

Hemker, et al., "Phenotyping the clotting system" Thromb Haemost, Nov. 2000, vol. 84, No. 5, pp. 747-751.

Hemker, et al., "Thrombin generation in plasma: its assessment via the endogenous thrombin potential" Thromb Haemost, Jul. 1995, vol. 74, No. 1, pp. 134-138.

Lipets, E.N., et al., Abstract Only "Integrated laboratory coagulation tests in hypercoagulation diagnosis and thrombosis risk assessment" Onxogematology, 2015, vol. 10, No. 3, pp. 73-91.

Lottermoser, et al., "The fibrinolytic system in chronic renal failure", Eur J Med Res, Sep. 28, 2001, vol. 6, No. 9, pp. 372-376.

Manco-Johnson, et al., "Heparin neutralization is essential for accurate measurement of factor VIII activity and inhibitor assays in blood samples drawn from implanted venous access devices", J Lab Clin Med, Jul. 2000, vol. 136, No. 1, pp. 74-79.

Meh, et al., "Disintegration and reorganization of fibrin networks during tissue-type plasminogen activator-induced clot lysis", Blood Coagul Fibrinolysis, Dec. 2001, vol. 12, No. 8, pp. 627-637.

Mosnier, et al., "The defective down regulation of fibrinolysis in hemophilia A can be restored by increasing the TAFI plasma concentration", Thromb Haemost, Oct. 2001, vol. 86, No. 4, pp. 1035-1039.

Palabrica, et al., Antifibrinolytic activity of apolipoprotein(a) in vivo: human apolipoprotein(a) transgenic mice are resistant to tissue plasminogen activator-mediated thrombolysis, Nat Med, Mar. 1995, vol. 1, No. 3, pp. 256-259.

Quiroga, et al., "Thrombin generation in plateletpoor plasma is normal in patients with hereditary mucocutaneous hemorrhages", Pathophysiol Haemost Thromb, 2003, vol. 33, No. 1, pp. 30-35.

Smith, et al., "A new euglobulin clot lysis assay for global fibrinolysis", Thromb Res, 2003, vol. 112, vols. 5-6, pp. 329-337.

Turecek, et al., Factor VIII inhibitor-bypassing agents act by inducing thron. bin generation and can be monitored b thrombin generation assay, Pathophysiol Haemost Thromb, 2003, vol. 33, No. 1, pp. 16-22.

Chapin, et al., "Fibrinolysis and the Control of Blood Coagulation", Blood Rev, Jan. 2015, vol. 29, No. 1, pp. 17-24.

Parasuraman, et al., "Venous Thromboembolism in Children", Circulation, Jan. 2006, vol. 113, pp. e12-e16.

Adam, et al., "D-dimer antigen: current concepts and future prospects", Blood, Mar. 26, 2009, vol. 113, No. 13, pp. 2878-2887.

Roger, et al., "Heart Disease and Stroke Statistics"—2012 Update: A Report From the American Heart Association Circulation, Jan. 3, 2012, vol. 125, No. 1, pp. e2-e220.

Di Nisio, et al., "Diagnostic accuracy of D-dimer test for exclusion of venous thromboembolism: a systematic review" J Thromb Haemost, Feb. 2007, vol. 5, No. 2, pp. 296-304.

Ginsberg, et al., "Sensitivity and Specificity of a Rapid Whole-Blood Assay for D-Dimer in the Diagnosis of Pulmonary Embolism", Ann Intern Med, Dec. 15, 1998, vol. 129, No. 12, pp. 1006-1011.

Ilich, A. et al., "Global assays of fibrinolysis," Int'l J. Lab. Hematol. 2017, vol. 39, No. 5, pp. 441-447.

Chitlur, M. "Challenges in the laboratory analyses of bleeding disorders." Thrombosis Res. 2012, vol. 130, No. 1, pp. 1-6.

Goldenberg, N.A., "A new global assay of coagulation and fibrinolysis." Thrombosis Res. 2005, vol. 116, No. 4, pp. 345-356.

| Patient history | Current anticoagulant regimen | Diagnosis of marked rise in coagulability by CloFAL assay | Change in antithrombotic therapy |
|---|---|---|---|
| VTE | None | Yes | *Escalate to prophylactic anticoagulation:*<br><br>-Enoxaparin 30-40mg or 0.5mg/kg subcutaneously every 12 hours<br>OR<br>-Enoxaparin 60 mg or 1mg/kg subcutaneously once-daily<br>OR<br>-Rivaroxaban 10 mg orally once-daily (or pediatric equivalent)<br>OR<br>-Apixaban 5 mg orally once-daily (or pediatric equivalent)<br>OR<br>-Apixaban 2.5 mg orally every 12 hours (or pediatric equivalent)<br>OR<br>-Warfarin orally once-daily to achieve INR 1.5-1.9 |
| VTE | Prophylactic regimen | Yes | *Escalate to therapeutic anticoagulation:*<br><br>-Enoxaparin 60 mg or 1mg/kg subcutaneously every 12 hours<br>OR<br>-Rivaroxaban 15 mg orally every 12 hours (first 3 weeks) or 20 mg orally once-daily (or pediatric equivalent)<br>OR<br>-Apixaban 5 mg orally every 12 hours (or pediatric equivalent)<br>OR<br>-Warfarin orally once-daily to achieve INR 2.0-3.0 |

USE OF A GLOBAL ASSAY OF COAGULATION AND FIBRINOLYSIS TO AIDE IN THROMBOEMBOLISM

REFERENCE TO RELATED APPLICATIONS

This application is a divisional of U.S. application Ser. No. 16/770,324, filed Jun. 5, 2020, which is a U.S. National Stage Application of International Application No. PCT/US2018/064233, filed on Dec. 6, 2018, which claims the benefit of U.S. Provisional Patent Application No. 62/595,910, filed on Dec. 7, 2017, which is hereby incorporated by reference for all purposes as if fully set forth herein.

STATEMENT OF GOVERNMENTAL INTEREST

This invention was made with government support under grant no. HL130048-01A1 awarded by the National Institutes of Health. The government has certain rights in the invention.

BACKGROUND OF THE INVENTION

Predicting and preventing catastrophic bleeding or excessive clotting ("thrombotic") episodes in patients with coagulation disorders remains a critical, and largely unrealized, medical challenge. Unlike individual molecular tests, assays that evaluate net clotting potential or the generation of (a) key enzymatic player(s) in the clotting system offer the potential to assist in the prediction of individual bleeding and thrombotic risk at a given point in time, and even the possibility to tailor a specific preventive medical approach to a particular patient based upon the net balance of his/her clotting system. Historically, such "global assays" have rarely been practical for clinical application. Over the past few years, technological advances have made the prospect of a clinically useful global assay more tenable. Yet, to date very few such global assays have been designed to evaluate both the clot formation ("coagulation") and clot breakdown ("fibrinolysis") abilities of the blood, each of which is an important component of the coagulation system. Defects in each of these functions have been found, for example, in severe hemophiliacs, as well as in a variety of bleeding and thrombotic disorders.

Despite many scientific advances in recent years to better understand bleeding and thrombotic disorders on the level of gene mutations, such diseases continue to cause long-term disability in a significant subset of patients. The ability to predict catastrophic bleeding or clotting episodes is an important goal for patients and their treating clinicians in order to maximize the potential for an enduring high level of patient functioning. This goal has remained largely elusive because individual molecular markers of coagulation do not provide an overall picture of an individual's hemostatic balance at a given time.

Knowledge of prognostic factors for recurrence in adult and pediatric venous thromboembolism (VTE) is limited. Elevated plasma levels of D-dimer (a marker of coagulation activation) following a 6-month course of anticoagulation in adults with unprovoked VTE are associated with a heightened risk of VTE recurrence, warranting prolonged therapy. In patients with provoked VTE, and in young VTE patients more generally, prognostic factors remain largely undefined.

SUMMARY OF THE INVENTION

Recently, using a global assay of clot formation and lysis (CloFAL) on plasma samples collected serially over time, the present inventor observed a phenomenon of rebound hypercoagulability which we now refer to as a paradoxical "marked rise in coagulability in the sub-acute period post-diagnosis of VTE" at 3 months post-diagnosis, relative to 4-6 weeks post-diagnosis, in a group of children with provoked VTE who were enrolled in a single-institution prospective inception cohort study.

The data provided by the inventive methods disclosed herein furthermore suggest that patients who manifest a "marked rise in coagulability" over time may add prognostic value in the prediction of recurrent thromboembolic events, beyond the prognostic value of an elevated D-dimer level. In the current standard of care, clinical decision making on duration of anticoagulation in the treatment of thromboembolism relies on the clinician's judgment regarding presence or absence of persistent hypercoagulability at the time of intended discontinuation of anticoagulation. Apart from use of the D-dimer test in selected circumstances, no laboratory methods exist to assist in this decision-making on duration of anticoagulation. In this manner, the inventive methods described herein support new paradigm for assisting in medical decision-making regarding duration of anticoagulation in the treatment and secondary prevention of thromboembolism.

Thus, in accordance with an embodiment, the present invention provides a method for identification or diagnosis of marked rise in coagulability in a subject who previously experienced a thrombotic event and underwent coagulation therapy comprising the steps of: a) analyzing a first biological sample taken from a subject at time period of about 4 to about 6 weeks post cessation of coagulation therapy using the CloFAL method and generating a CloFAL maximum amplitude value; b) analyzing a second biological sample taken from a subject at time period of about at least 2 months post cessation of coagulation therapy using the CloFAL method and generating a CloFAL maximum amplitude value; c) comparing the CloFAL maximum amplitude value of a) to b); and d) identifying the subject as being at risk for paradoxical marked rise in coagulability when the CloFAL maximum amplitude value of b) is at least 50% greater than the CloFAL maximum amplitude value of c).

In accordance with a further embodiment, the present invention provides for a method for prevention or treatment of thrombosis or a thrombotic event a subject who previously experienced a thrombotic event and underwent anticoagulation therapy and exhibits a marked rise in coagulability wherein a biological sample from the subject was analyzed using the CloFAL method at time period of about 4 to about 6 weeks, and subsequently about 3 months, post-diagnosis of VTE, and wherein the CloFAL maximum amplitude value of the sample at about 3 months post-diagnosis of VTE was at least 50% greater than the CloFAL maximum amplitude value of the sample at about 4 to about 6 weeks post-diagnosis of VTE.

In accordance with another embodiment, the present invention provides a method for prevention or treatment of thrombosis or a thrombotic event in a subject who previously experienced a thrombotic event and underwent anticoagulation therapy who is at risk for a marked rise in coagulability, comprising the steps of: a) analyzing a first biological sample taken from a subject at time period of about 4 to about 6 weeks post-diagnosis of VTE using the CloFAL method and generating a CloFAL maximum amplitude value; b) analyzing a second biological sample taken from a subject at time period of about 3 months post-diagnosis of VTE using the CloFAL method and generating a CloFAL maximum amplitude value; c) comparing the CloFAL maximum amplitude value of a) to b); d) identifying the subject as having a marked rise in coagulability when the CloFAL maximum amplitude value of b) is at least 50% greater than the CloFAL maximum amplitude value of a); and e) administering to the subject an appropriate antithrombotic therapeutic regimen, including prolonged duration and/or increased intensity of anticoagulation and/or the administration of adjunctive immunomodulatory therapies.

In accordance with another embodiment, the present invention provides a method for identification or diagnosis of who is at risk for a marked rise in plasma coagulability in a subject who previously experienced a thrombotic event and underwent coagulation therapy comprising the steps of: a) analyzing a first biological sample taken from a subject at time period of about 6 weeks +/−2 weeks prior to planned cessation of anticoagulation therapy using the CloFAL method and generating a CloFAL maximum amplitude value; b) analyzing a second biological sample taken from a subject at time of planned cessation (or within about 2 weeks of post-cessation) of anticoagulation therapy using the CloFAL method and generating a CloFAL maximum amplitude value; c) comparing the CloFAL maximum amplitude value of a) to b); and d) identifying the subject as having a marked rise in coagulability and hence being at heightened risk for recurrent thromboembolism when the CloFAL maximum amplitude value of b) is at least 50% greater than the CloFAL maximum amplitude value of a).

In accordance with another embodiment, the present invention provides a method for identification or diagnosis of who is at risk for a marked rise in plasma coagulability in a subject who previously experienced a thrombotic event and underwent anticoagulation therapy comprising the steps of: a) analyzing a first biological sample taken from a subject at time period of about 6 weeks +/−2 weeks prior to planned cessation of anticoagulation therapy using the CloFAL method and generating a CloFAL maximum amplitude value; b) analyzing a second biological sample taken from a subject at time of planned cessation (or within about 2 weeks of post-cessation) of anticoagulation therapy using the CloFAL method and generating a CloFAL maximum amplitude value; c) comparing the CloFAL maximum amplitude value of a) to b); and d) identifying the subject as having a marked rise in coagulability and hence being at heightened risk for recurrent thromboembolism when the CloFAL maximum amplitude value of b) is at least 50% greater than the CloFAL maximum amplitude value of a); and e) administering to the subject an appropriate antithrombotic therapy regimen.

BRIEF DESCRIPTION OF THE DRAWINGS

FIG. 2. Serial CloFAL assay waveforms at 4-6 weeks and 3 months post-event in two exemplary children with provoked VTE. In each panel, the pooled normal plasma standard is shown for reference (FACT curve). The patient's samples are run in triplicate and absorbance data is then averaged at each time point for the triplicate plasma wells (Cumulative curve). Panel A: 14 y.o. male with a provoked lower extremity DVT. CloFAL assay maximum amplitude (MA) and $AUC_{60}$, as measures of global hypercoagulability, were both elevated acutely (4-6 weeks) but normalized by the 3 month post-DVT sampling (MA 0.32 and 0.23 at 4-6 weeks and 3 months respectively; AUC60 12.9 and 8.8 at 4-6 weeks and 3 months respectively). Panel B: 15 y.o. male with a central venous catheter-associated upper extremity DVT. CloFAL assay shows an increase in MA >50% at the 3 months relative to the 4-6 weeks post-DVT period consistent with a marked rise in coagulability (MA 0.25 and 0.45 at 4-6 weeks and 3 months respectively).

DETAILED DESCRIPTION OF THE INVENTION

In various embodiments, parameters of clotting and/or fibrinolysis derived from the disclosed methods may be "used for the detection, diagnosis and/or prognosis of various disease states that affect hemostatic balance, such as hemophilia, von Willebrand's disease and other bleeding or prothrombotic conditions. The disclosed methods are of use to assess an individual's prothrombotic and/or hemorrhagic tendencies in a wide variety of conditions, such as trauma, acute coronary events/syndromes, cardiac bypass, organ transplantation, intensive care, diagnostic surgical biopsies, or other surgical or medical procedures.

In accordance with some embodiments, the present invention relates to methods and compositions for evaluating clot formation and fibrinolysis in a sample from a subject who previously experienced a thrombotic event and underwent anticoagulation therapy.

In accordance with some other embodiments, the present invention relates to methods and compositions for evaluating clot formation and fibrinolysis in a sample from a subject who previously experienced a thrombotic event but who never received anticoagulation therapy (refused or had contraindications at the time), and exhibits a rise in coagulability over time by CloFAL assay, and therefore should be reassessed for (or reconsider) initiating anticoagulation.

As used herein, the term "marked rise in coagulability" means that, among subjects who were placed on anticoagulation therapy due to a thrombotic event or surgery, a proportion of such patients show a marked increase over time in CloFAL assay parameters that measure coagulative potential in plasma. In some embodiments, the CloFAL assay parameter which significantly correlate with paradoxical marked rise in coagulability is the maximum amplitude of the CloFAL waveform, or (MA).

As used herein, the term "treatment" or "treating" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level. In accordance with some embodiments, the disease or condition being treated is related to disease states that affect hemostatic balance, such as hemophilia, von Willebrand's disease and other bleeding or prothrombotic conditions.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates. Ceboids, or Simoids (monkeys) or of the order Anthropoids (humans and apes). An especially preferred mammal is the human.

In accordance with some embodiments, the subject is a human. In other embodiments, the subject is a juvenile or adolescent with an age of less than 21 years.

In accordance with some embodiments of the present invention, it will be understood that the term "biological sample" or "biological fluid" includes, but is not limited to, any quantity of a substance from a living or formerly living patient or mammal. Such substances include, but are not limited to, blood, serum, plasma, urine, cells, organs, tissues, bone, bone marrow, lymph, lymph nodes, synovial tissue, chondrocytes, synovial macrophages, endothelial cells, and skin. In a preferred embodiment, the fluid is blood or serum.

Thus, in accordance with an embodiment, the present invention provides a method for identification or diagnosis of a marked rise in plasma coagulability in a subject who previously experienced a thrombotic event and underwent anticoagulation therapy, comprising the steps of: a) analyzing a first biological sample taken from a subject at time period of about 4 to about 6 weeks post-diagnosis of VTE using the CloFAL method and generating a CloFAL maximum amplitude value; b) analyzing a second biological sample taken from a subject at time period of about a 3 months post-diagnosis of VTE using the CloFAL method and generating a CloFAL maximum amplitude value; c) comparing the CloFAL maximum amplitude value of a) to b); and d) identifying the subject as being at risk for recurrent VTE when the CloFAL maximum amplitude value of b) is at least 50% greater than the CloFAL maximum amplitude value of a).

In accordance with a further embodiment, the present invention provides for a method for prevention or treatment of thrombosis or a thrombotic event in a subject who previously experienced a thrombotic event and underwent anticoagulation therapy who is at risk for a marked rise in plasma coagulability (and has a consequently heightened risk of recurrent VTE), wherein a biological sample from the subject was analyzed using the CloFAL method at time period of about 4 to about 6 weeks, and subsequently approximately 3 months, post-diagnosis of VTE, and wherein the CloFAL maximum amplitude value of the sample at approximately 3 months post-diagnosis of VTE was at least 50% greater than the CloFAL maximum amplitude value of the sample of time period of about 4 to about 6 weeks post-diagnosis of VTE.

In accordance with another embodiment, the present invention provides a method for prevention or treatment of thrombosis or a thrombotic event in a subject who previously experienced a thrombotic event and underwent anticoagulation therapy who is at risk for a marked rise in plasma coagulability (and has a consequently heightened risk of recurrent VTE), comprising the steps of: a) analyzing a first biological sample taken from a subject at time period of about 4 to about 6 weeks post-diagnosis of VTE using the CloFAL method and generating a CloFAL maximum amplitude value; b) analyzing a second biological sample taken from a subject at time period of about 3 months post-diagnosis of VTE, using the CloFAL method and generating a CloFAL maximum amplitude value; c) comparing the CloFAL maximum amplitude value of a) to b); d) identifying the subject as being at risk for rebound hypercoagulability when the CloFAL maximum amplitude value of b) is at least 50% greater than the CloFAL maximum amplitude value of a); and e) administering to the subject an appropriate antithrombotic therapy regimen.

In some embodiments, the time for the second or later measurement of CloFAL maximum amplitude value is at least 3 months post-diagnosis of VTE. In other embodiments, the time period can be 4, 5, 6, 8, 10, 12 months, 18 months, 24 months, or longer after diagnosis of VTE.

In accordance with another embodiment, the present invention provides a method for identification or diagnosis of who is at risk for a marked rise in plasma coagulability in a subject who previously experienced a thrombotic event and underwent coagulation therapy comprising the steps of: a) analyzing a first biological sample taken from a subject at time period of about 6 weeks +/−2 weeks prior to planned cessation of anticoagulation therapy using the CloFAL method and generating a CloFAL maximum amplitude value; b) analyzing a second biological sample taken from a subject at time of planned cessation (or within about 2 weeks of post-cessation) of anticoagulation therapy using the CloFAL method and generating a CloFAL maximum amplitude value; c) comparing the CloFAL maximum amplitude value of a) to b); and d) identifying the subject as being at risk for a rise in plasma coagulability when the CloFAL maximum amplitude value of b) is at least 50% greater than the CloFAL maximum amplitude value of a).

In accordance with another embodiment, the present invention provides a method for identification or diagnosis of who is at risk for a marked rise in plasma coagulability in a subject who previously experienced a thrombotic event and underwent coagulation therapy comprising the steps of: a) analyzing a first biological sample taken from a subject at time period of about 6 weeks +/−2 weeks prior to planned cessation of anticoagulation therapy using the CloFAL method and generating a CloFAL maximum amplitude value; b) analyzing a second biological sample taken from a subject at time of planned cessation (or within about 2 weeks of post-cessation) of anticoagulation therapy using the CloFAL method and generating a CloFAL maximum amplitude value; c) comparing the CloFAL maximum amplitude value of a) to b); and d) identifying the subject as being at risk for a rise in plasma coagulability when the CloFAL maximum amplitude value of b) is at least 50% greater than the CloFAL maximum amplitude value of a); and e) administering to the subject an appropriate antithrombotic therapy regimen.

In some embodiments, the time for the second or later measurement of CloFAL maximum amplitude value is at least 3 months post-cessation of coagulation therapy. In other embodiments, the time period can be 1, 2, 4, 5, 6, 8, 10, 12 months, 18 months, 24 months, or longer after cessation of coagulation therapy.

In accordance with the methods disclosed herein, the methods for determination of evaluating clot formation, overall coagulability, and fibrinolysis in a sample are encompassed in a method designated as Clot Formation and Lysis (CloFAL) assay, as disclosed in International Patent Application No. WO2006036744, entitled "METHODS FOR A GLOBAL ASSAY OF COAGULATION AND FIBRINOLYSIS" and incorporated by reference herein as if set forth in its entirety.

The CloFAL methods used in the inventive methods are described briefly herein. A clot is formed in a sample of blood or plasma and thereafter the clot is lysed. The kinetic parameters for formation and lysis of the clot are determined, preferably using a spectrophotometric assay, to assess the individual's net hemostatic balance at a given time, allowing prothrombotic and hemorrhagic risk assessment. In another embodiment, measured parameters can include the maximum amplitude (MA) of spectrophotometric absorbance, the time to maximum turbidity (T1), the time to completion of the first phase of decline in turbidity (T2), and the area under the curve (AUC) over measured time intervals. From such measurements, the coagulation index (CI) and fibrinolytic index (FI) and modified Fibrinolytic Index ($FI_2$) may be determined. CI, FI, AUC and/or individual measured CloFAL parameters are of use to detect or diagnose prothrombotic and/or hemorrhagic diseases or conditions and to develop therapeutic treatments tailored to the individual's net hemostatic balance.

In certain embodiments, involving continuous measurement of clot lysis and clot formation in a sample, the information obtained is more comprehensive and more directly related to actual physiological conditions for clot formation and lysis in the body than presently available assays. The disclosed methods and compositions allow the rapid and inexpensive assessment of the hemostatic balance in an individual over time.

In one embodiment, clot formation and fibrinolysis may be performed in a container or test cell, including but not limited to 96-well microtiter plates, into which a sample (e.g. fresh or freeze-thawed, platelet-poor plasma) and appropriate reagents have been added. An exemplary apparatus of use may include a sample, one or more reagents, buffer, a reagent chamber, and a detection instrument, such as a spectrophotometer. In more particular embodiments, the reagents added to the reagent chamber may include small amounts of tissue factor (TF), lipidated TF, and/or tissue-type plasminogen activator (tPA). Where exemplary containers exhibit multiple sample compartments, such as a 96-well plate, the sample may preferably be analyzed in replicates, such as duplicate or triplicate wells of a 96-well plate. An advantage of the disclosed methods is that the amount of sample required to assay may be relatively small, for example 75 µL of plasma sample per well.

Samples may also include a blank well containing only reagent for comparison with the test samples. Samples may further comprise one or more cellular entities, such as white blood cells and/or endothelial cells, in suspension or in a monolayer. The plate may be analyzed in an automated, thermoregulated (37° C.) spectrophotometer and the course of clot formation and subsequent lysis may be monitored as continuous changes in the absorbance of the specimen over a course of time, for example, over three hours. In a preferred embodiment, optical density at 405 nm or dual wavelength OD (405 and 630 nm) may be monitored continuously or at selected frequent time intervals. The spectrophotometer preferably is interfaced with a computer to permit analysis of kinetic OD measurements using (a) data analysis program(s). A curve may be generated over the course of the assay reactions that include an initial baseline OD, followed by a progressive rise in optical density to a point of maximum OD, then completed by a progressive decline in optical density to baseline. A plasma standard (preferably pooled plasma from healthy individuals) and controls (preferably one normal and one to two abnormal controls each, for coagulative function and fibrinolytic function) may be run simultaneously with the clinical/laboratory sample(s) using the same protocol.

A clotting curve may be generated whereby coagulation and fibrinolytic parameters of the plasma sample are obtained, relative to a simultaneously run pooled normal subject plasma standard. Specific measurements may include the lag time (the time from assay initiation to time to clot initiation, as measured by rise in OD above baseline or a specified threshold), the maximum amplitude (MA) (maximum OD minus baseline OD), the time to maximum turbidity (T1), the area under the curve (AUC) over the course of measured time intervals, and the area over the curve (AOC) over the course of measured time intervals (e.g., from T1 to 10-30 minutes thereafter, during the phase of decline in OD. A coagulation index (CI) may be calculated, in one example, as the AUC over the course of the first 30 minutes of an assay, referenced to a plasma standard. A fibrinolytic index (FI) may be calculated, for example, by relating the ratio of T2 to T1 for a sample as compared to a standard, with a correction factor for differences in maximum OD, as discussed below. Alternatively, a modified FI ($FI_2$) may be calculated by the area above the curve, or a reciprocal AUC, from T1 to up to T1+30 minutes for a sample compared to a standard, with a correction factor as above. Specimens may be compared between normal controls and patients suspected of having, or known to have, one or more pathologic conditions, such as hemophilia or other diseases relating to clotting and or clot lysis.

Particular details of exemplary embodiments of CloFAL assays are provided in the Examples below. However, the skilled artisan will realize that the concentrations of various reagents and times and temperatures of reactions may be varied from those specified below without undue experimentation by the person of ordinary skill in the art. Further, where various factors, such as calcium, TF and tPA are disclosed, such factors may be substituted or supplemented with alternative factors known in the art to exhibit similar activities, within the scope of the claimed methods and compositions.

The CloFAL global assay is reproducible and analytically sensitive to deficiencies and excesses of key components in the coagulation and fibrinolytic systems, as well as to physiologic alterations in hemostasis. The measurement of these parameters may be applied to assess subjects with known and/or as yet undefined hemorrhagic and prothrombotic conditions.

In one embodiment, any of the combination CloFAL assay results may be analyzed in an individual suffering from a heart condition. Non-limiting examples of heart conditions include but are not limited to myocardial ischemia, myocardial infarction, acute coronary syndromes, atherosclerotic coronary artery disease, valvular disease, and congestive heart failure.

In another embodiment, any of the combination CloFAL assay results may be analyzed in an individual suffering from a prothrombotic condition. Examples of prothrombotic conditions include but are not limited to venous or arterial thromboembolism, including stroke, as well as hypercoagulable states (in particular, factor V Leiden and prothrombin 20210 mutations, antiphospholipid antibodies, anticoagulant deficiency, and elevated levels of procoagulant factors, homocysteine, or lipoproteins).

In certain embodiments, any of the combination CloFAL assay results may be analyzed in an individual suffering from a bleeding condition, or at risk for severe perioperative bleeding. Non-limiting examples of bleeding conditions include the hemophilias and other coagulation factor deficiencies or dysfunctions (including a/hypo/dysfibrinogenemia), von Willebrand disease, platelet function abnormalities and fibrinolytic abnormalities (e.g., PAI-I deficiency). A non-limiting example of settings of risk for severe perioperative bleeding include adolescents with idiopathic scoliosis undergoing posterior spinal fusion surgery, in which overall coagulative capacity in plasma, as measured pre-operatively using the CloFAL assay coagulation index assists in the pre-operative identification of patients who are at heightened risk for severe intra-operative bleeding and/or who are at heightened risk for requiring intra/post-operative blood transfusion.

In yet another embodiment, any of the combination CloFAL assay results may be analyzed in healthy children and adults to assess bleeding and/or prothrombotic risk in the steady state and in times of altered (pathologic or physiologic) coagulation and/or fibrinolysis, including the special physiologic states of pregnancy and the neonatal period. Any combination of CloFAL assay may be used as a pre-operative or pre-treatment screening test on a sample from a test subject; in addition, any combination of CloFAL assay may be used as a post-operative or post-treatment test on a sample from a test subject.

The CloFAL assay described here was modified from those of He et al. (1999) and Smith et al. (2003). As compared to that by Smith et al., which evaluates only fibrinolysis, the CloFAL assay permits assessment of coagulability as well. In the method of Smith et al., clotting is artificially induced immediately in the assay and hence coagulative function (i.e., coagulability) is unable to be measured, as is consistent with that assay's unique purpose and role in assessing fibrinolytic function. Furthermore, when compared to the global assay of He et al., the CloFAL assay permits testing with a single reagent to evaluate both coagulation and fibrinolysis, rather than requiring (as does that of He et al.) the preparation of two distinct reagents for separate evaluation of the plasma sample. In addition, unlike the assay of He et al., the CloFAL assay does not require the use of thrombin (a key end-product of the coagulation reactions) among the assay reagents. Neither the method of He et al. nor that of Smith et al. is envisioned or shown to detect a marked rise in plasma coagulability post-diagnosis of VTE, nor to identify those VTE patients who are at risk for recurrent VTE. In the CloFAL assay, frozen plasma aliquots are thawed prior to assay, for example in a 37° C. water bath for three minutes. Comparison of freeze-thawed versus fresh platelet-poor plasma specimens from the same individual have revealed no differences in the CloFAL curve. Plasma samples (fresh or freeze-thawed) can be maintained for up to 30 minutes in an ice-water bath until time of assay. For preparation of reactant solution, recombinant lipidated human TF (American Diagnostica, Stamford, CT; 0.5 μg/mL stock solution prepared according to manufacturer instruction) and two-chain recombinant tPA (American Diagnostica, Stamford, CT; 0.5 mg/mL) are added to a stock solution of Tris-buffered saline (TBS; 66 mM Tris, 130 mM NaCl, pH=7.0) containing 34 mM $CaCl_2$, to a concentration of 4 pM and 900 ng/mL, respectively (final concentrations of 2 pM lipidated TF and 450 ng/mL tPA after addition of reactant solution to plasma sample, as described below).

In accordance with another embodiment of the assay, phospholipid and TF can be used as separate reagents, as an alternative to using lipidated TF, TBS stock solutions can be stored for up to one month at 4° C., and reconstituted stock solutions of tPA and lipidated TF can be stored for up to one month (and at least 24 hours) at −70° C., for use in preparation of fresh reactant solution. The reactant solution is maintained at room temperature until time of assay, not to exceed 30 minutes.

Uses of CloFAL Assay for Evaluating and Monitoring Fibrinolytic Capacity

Whether or not cell destruction can be minimized after physiological events such as myocardial infarctions, stroke or gangrene may depend, in part, upon the existence of pathological or therapeutically induced fibrinolysis. In order to eliminate or minimize such cell destruction in an individual who has undergone or is undergoing a stroke, heart attack or similar event, it would be useful to rapidly ascertain whether the individual's clot lysis ability is within a normal range of lytic response times. By comparing the individual's specific lytic response time to an average lytic response time of a normal, non-pathogenic individual, or within a given individual over time, a treating physician may determine whether the patients specific lytic response capability needs to be treated or otherwise taken into consideration.

Under conditions in which arterial or venous thrombosis has occurred or is likely to occur, such as during and after surgery, it becomes critical that the treating physician has reliable information available about an individual's fibrinolytic processes. For example, pathological thrombus formation is especially likely to occur during cardiac surgery utilizing extra-corporeal passage of blood. Although clotting during cardiac surgery may be minimized through use of heparin or other anticoagulants, a surgical patient's natural lytic ability can help avoid surgical complications by dissolving any pathological thrombi that form. If a particular surgical patient's lytic ability is impaired, a physician may elect to administer thrombolytic agents to maintain a particular level of lytic activity and to avoid the possibility of permanent and disabling clot formation occurring during surgery. To maintain a desired level of lytic activity, it would be useful to assess whether the administration of a thrombolytic agent had the desired effect upon the surgical patient.

Furthermore, when a deep venous thrombosis or pulmonary embolism is veno-occlusive and/or extensive, compromising venous or pulmonary function or risking chronic venous insufficiency due to venous valvular damage, thrombolytic therapy may be indicated. Such therapy would be better monitored (and its bleeding complications potentially minimized) through use of an assay designed to measure fibrinolytic capacity of plasma at a given time or within a selected time period, such as pre-treatment, during treatment, or post-treatment.

Generally, in the CloFAL global assay, blood is collected with the child or adult participant at rest in the seated position by atraumatic peripheral venipuncture technique with minimal applied stasis. Samples are collected into BD Vacutainer, 3.2% buffered sodium citrate, siliconized blood collection tubes (Becton-Dickinson, Franklin Lakes, NJ) or similar citrated blood collection tubes, with collection of the initial 1 mL of blood into a discard tube. All specimens are centrifuged for 15 minutes at 4° C. and 2500×g, and the plasma supernatant is then centrifuged for an additional 15 minutes to remove any residual platelets. All samples are aliquoted into 1.5 mL polypropylene long-term freezer storage tubes with O-ring screw caps (USA Scientific, Ocala, FL) or similar long-term freezer storage tubes and stored at −80° C. until time of assay.

The CloFAL assay permits testing with a single reagent to evaluate both coagulation and fibrinolysis. In addition, the CloFAL assay does not require the use of thrombin (a key end-product of the coagulation reactions) among the assay reagents. Frozen plasma aliquots are thawed prior to assay, for example in a 37° C. water bath for three minutes. Plasma samples (fresh or freeze-thawed) can be maintained for up to 30 minutes in an ice-water bath until time of assay. For preparation of reactant solution, recombinant lipidated human TF (American Diagnostica, Stamford, CT; 0.5 μg/mL stock solution are prepared according to manufacturer instruction) and two-chain recombinant tPA (American Diagnostica, Stamford, CT; 0.5 mg/mL) are added to a stock solution of Tris-buffered saline (TBS; 66 mM Tris, 130 mM NaCl, pH=7.0) containing 34 mM CaCl$_2$, to a concentration of 4 pM and 900 ng/mL, respectively (final concentrations of 2 pM lipidated TF and 450 ng/mL tPA after addition of reactant solution to plasma sample, as described below). TBS stock solutions were stored for up to one month at 4° C., and reconstituted stock solutions of tPA and TF were stored for up to one month (and at least 24 hours) at −80° C., for use in preparation of fresh reactant solution. The reactant solution was maintained at room temperature until time of assay, not to exceed 30 minutes.

Figure 1:
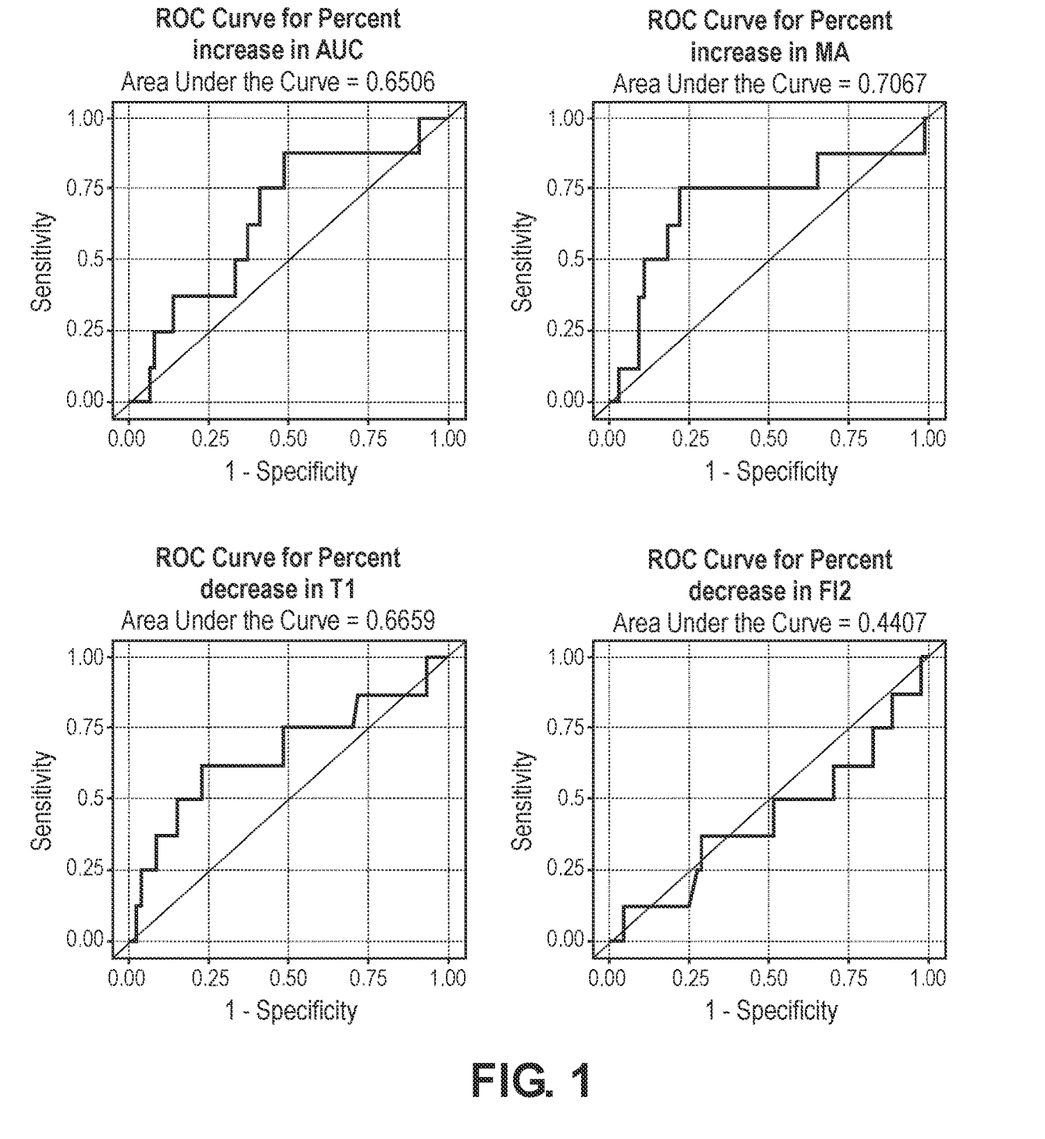
FIG. 1. Receiver operating characteristic curves for subacute percent change (measurements at 3 months vs. 4-6 weeks post-diagnosis of index VTE) in CloFAL assay parameters.

For each patient sample to be analyzed 75 μL of freeze-thawed or fresh plasma was dispensed into each of three wells in a round-bottom, 96-well, Nunc assay plate (Fisher Scientific, Santa Clara, CA), and then pre-warmed at 37° C. for three minutes. Using a multi-tip automated pipette, 75 μL of reactant solution was added simultaneously to each well. The plate was then immediately placed in a thermoregulated multi-channel microplate spectrophotometer (for example, PowerWave HT, Bio-Tek Instruments, Winooski, VT) for dual kinetic absorbance measurements at 405 nm and 630 nm at serial (for example, 45-second) intervals for one or more (for example, 3) hours, following an initial five-second mixing step prior to the first reading. The spectrophotometer interfaced with a computer such that all its operations, including continuous analysis of delta-absorbance (405 nm minus 630 nm) data using KC4™ PC or other instrument-specific software, may be automated. As shown in FIG. 1, beginning at time zero (T0), a curve is generated over the course of the assay reactions that had an initial baseline absorbance, followed by a progressive rise in absorbance to a point of maximum absorbance (achieved at T1), then a first phase of decline in absorbance (ending at T2, the time point at which the slope of decline in absorbance changes by +0.10 mOD/min), and completed by a further decline in absorbance to baseline.

The kinetic absorbance data is exported to Microsoft Excel or other data analytic software. Using the absorbance data in each triplicate well (or other replicate number of wells) of a given plasma specimen, the maximum amplitude of rise in absorbance is determined (MA=maximum absorbance minus baseline absorbance, where baseline absorbance was obtained by averaging the third through eighth kinetic readings). The MA values from the replicate wells are then averaged to generate an MA value for the specimen. T1 and T2 were also obtained, and averaged from the replicate wells to generate T1 and T2 values for the specimen. In one example using the area under the curve (AUC) over the course of the initial 30 minutes of the assay, a coagulation index (CI) can be calculated that relates this value for the sample to that of the standard run with each assay (FACT, George King Biomedical, Overland Park, KS), as follows:

$$CI = \frac{(AUC_{0\ through\ 30\ min})_{sample}}{(AUC_{0\ through\ 30\ min})_{standard}} \times 100$$

A fibrinolytic index (FI) is calculated by relating the ratio of the time to completion of the first phase of decline in absorbance (T2) to the time to maximum absorbance (T1) for the sample as compared to the standard, with a correction factor for differences in maximum absorbance (MA$_{standard}$/MA$_{sample}$), as follows:

$$AUC_{60} = \frac{(AUC_{0\ through\ 60\ min})_{sample}}{(AUC_{0\ through\ 60\ min})_{standard}} \times 100$$

CI and FI are each reported as averaged values among the replicate wells.

A modified FI is calculated as follows (where AOC=area over the curve):

$$FI = \frac{T2(T1^*MA)_{sample}}{T2(T1^*MA)_{standard}} \times 100$$

As an additional index of coagulability, cumulative AUC for the first 60 minutes of the assay (AUC$_{60}$) as a percent of the standard, are also calculated. In particular, AUC$_{60}$ (with calculation provided below) has been observed to be associated with hypercoagulability and thrombotic tendency:

$$FI_2 = \frac{AOC_{(T1\ through\ T1+20\ min)sample}}{MA_{sample}}$$

In summary, the CloFAL curve of each plasma specimen is analyzed for MA, T1, T2, CI, FI and/or FI$_2$, and AUC$_{60}$.

CloFAL parameters may be measured in age-specific healthy control subpopulations for the establishment of normative reference values, and may also be measured in disease-specific groups at baseline/steady-state clinical status for the establishment of disease-specific reference ranges in this state. These reference ranges then serve as the basis for determination of a given subject's plasma coagulative and fibrinolytic functions at a given time via CloFAL assay as normal versus abnormal relative to healthy and/or similarly-diseased individuals, and if abnormal, whether indicating a tendency toward hypo-versus hypercoagulability and hypo-versus hyperfibrinolysis, and hence a tendency toward thromboembolism versus pathological bleeding. In addition, a given subject's plasma coagulative and fibrinolytic functions at a given time may each be assessed by CloFAL assay as increased versus decreased relative to another clinically-informative time point in which that subject's plasma coagulative and fibrinolytic functions were, or will be, assess by CloFAL assay, toward the determination of relative changes in intra-individual tendency toward thromboembolism versus pathological bleeding.

In accordance with some embodiments, the present inventive methods provide a means for identifying or diagnosing a subject with an increased risk of a thrombotic event and/or marked rise in plasma coagulability over time. In such instances, the subject is then placed on an appropriate treatment regimen to prevent a new thromboembolism.

Figure 3:
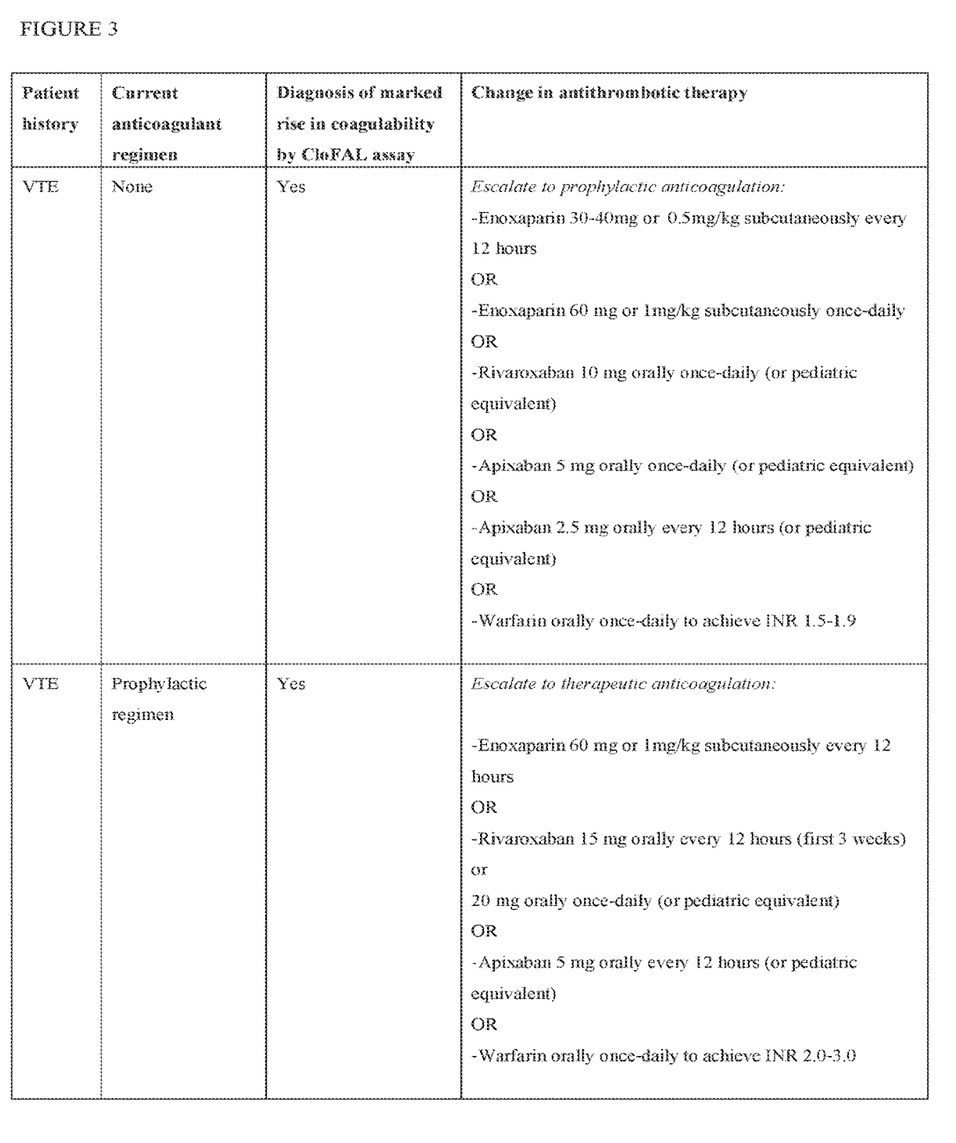
FIG. 3. A table comprising a number of differing non-limiting examples of treatment regimens used in connection with the identification of a marked rise in coagulability in a subject, using the methods described herein.

As used herein, the term "antithrombotic therapy regimen" can comprise a number of differing regimens including, but not limited to, an effective frequency and intensity of anticoagulation, including oral, subcutaneously injectable, or intravenous anticoagulants. Non-limiting examples of oral anticoagulants include vitamin K antagonists, direct factor Xa inhibitors, and direct thrombin inhibitors. Non-limiting examples of subcutaneously injectable anticoagulants include low molecular weight heparins and synthetic pentasaccharides. Non-limiting examples of intravenous anticoagulants include unfractionated heparin and direct thrombin inhibitors. Non-limiting examples of such treatment regimens used in connection with the assay described herein are shown in the table in FIG. 3.

In the circumstance of the determination of a marked rise in plasma coagulability by CloFAL assay during the sub-acute period post-diagnosis of VTE, examples of potential changes in anticoagulant management aimed at mitigating the heightened risk of recurrent VTE include increasing the dose of the existing anticoagulant agent, and/or prolonging the course of the existing anticoagulant treatment, and/or adding immunomodulatory therapies to the existing anticoagulant treatment in the setting of clinical knowledge or clinical suspicion of a systemic inflammatory or autoimmune contribution to the marked rise in plasma coagulability. Non-limiting examples of such adjunctive immunomodulatory therapies include corticosteroids, calcineurin inhibitors, inosine monophosphate dehydrogenase inhibitors, and anti-interleukin monoclonal antibodies, It will be understood by those of skill in the art, that the inventive methods also include monitoring the subject post-treatment, and during follow-up preventative treatment. until the subject's CloFAL MA levels are considered to be in the normal range or to have returned to the subject's baseline (or in the case of the period several months post-diagnosis of VTE, to have returned to less than a 50% increase in the CloFAL MA value obtained at 4-6 weeks post-diagnosis of VTE).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in an unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Clinical data and banked plasma specimens were combined from an ongoing NHLBI-sponsored multinational multicenter trial of VTE treatment in patients <21 years old (the Kids-DOTT trial) with those from a single-institutional prospective cohort study of VTE in patients <21 years old at Johns Hopkins All Children's Hospital (St. Petersburg, FL, USA). The CloFAL global assay was performed as previously described, on banked plasma samples from 4-6 weeks and 3 months post-diagnosis of acute VTE, with heparin pre-treatment of samples prior to assay.

Study Design

This study combined clinical data and banked plasma biospecimens collected at 4-6 weeks and 3 months post-diagnosis of provoked VTE in the pediatric VTE cohort of the Johns Hopkins All Children's (St. Petersburg, FL) institution-wide prospective inception multi-cohort and biobanking study (iPICS) with that from the NHLBI-sponsored Kids-DOTT trial. In many cases, these two time points simultaneously represented 6 weeks +/−2 weeks prior to planned cessation of anticoagulation and time of planned cessation (or within 2 weeks post-cessation) of anticoagulation, respectively. The study was approved by the local Institutional Review Board at each participating site, with signed informed consent/assent required for patient participation.

The Kids-DOTT trial design has also been previously reported in detail (Goldenberg N A, Abshire T, Blatchford P J, Fenton L Z, Halperin J L, Hiatt W R, et al. Multicenter randomized controlled trial on Duration of Therapy for Thrombosis in Children and Young Adults (the Kids-DOTT trial): pilot/feasibility phase findings. J Thromb Haemost. 2015; 13(9):1597-605; Bernard T J, Armstrong-Well J, Goldenberg N A. The institution-based prospective inception cohort study: design, implementation, and quality assurance in pediatric thrombosis and stroke research. Semin Thromb Hemost. 2013; 39(1):10-14). The present study included patients enrolled in the iPICS VTE cohort from 2013 through 2016 and in Kids-DOTT from 2007 through 2016.

Blood Sample Collection, Processing, and Preparation for Laboratory Analyses

Whole blood was collected at follow-up visits 4-6 weeks and 3 months post-diagnosis of VTE via atraumatic peripheral venipuncture using minimal applied stasis into BD Vacutainer 3.2% buffered sodium citrate siliconized blood collection tubes. Sample processing occurred within 1 hour from collection. Samples were centrifuged at 2500 g for 15 minutes at 4° C., afterwards the supernatant was isolated and subjected to repeat centrifugation for 15 minutes at the aforementioned settings. The resulting platelet-poor plasma supernatant was pooled, aliquoted into propylene tubes, and frozen at −80° C. in SAM units (Hamilton®, Reno, Nevada, USA) of the College of American Pathologists-accredited JHACH Pediatric Biorepository for long-term storage until time of assay. All plasma aliquots undergoing CloFAL assay analysis were heparinase-treated once thawed in preparation for the assay.

Kids-DOTT Trial Assessments

Study participation was expected to last for 2 years. Many of the assessments in this study were completed as part of the standard of care visits. The study comprised the following: Review of scans of the blood clot performed at diagnosis and at approximately 6 weeks after diagnosis; Randomization to either 6 weeks or 3 months duration of blood thinner treatment; Blood sample collection for research at 6 weeks and 3 months post-diagnosis; Brief follow-up phone calls at 2, 4 and 5 months following diagnosis; In-person follow-up at 6 weeks, and 3, 6, 12, and 24 months, after diagnosis; Treatment diary to track when doses of the participants blood clot medication are missed; Tracking of medical events that happen to the participant;

Study Participation Requirements: Recently diagnosed, for the first time, with an acute venous thrombosis; Age less than 21 years old at time of diagnosis of blood clot; Planned (or already on) treatment for the acute blood clot; No history of cancer; No prior history of treated blood clots.

Those few patients (n=3) who received agents other than low molecular weight heparin at these time points were excluded. Assay measurements included maximal amplitude of the CloFAL waveform (MA), time to maximal amplitude (T1), and area under the curve at 60 minutes, indexed to that of the pooled normal plasma standard ($AUC_{60}$). For each patient, the change in each CloFAL parameter between the 3 months and the 4-6 week post-VTE time points was then calculated.

Statistical Analyses

Descriptive statistics were used to summarize data on patient characteristics and outcomes. For each patient, the percentage change in each CloFAL parameter (MA, T1, $AUC_{0-60}$ min and $FI_2$) was calculated between the 3 month and the 4-6 week sample post-diagnosis of index VTE. We planned to employ receiver operating characteristics (ROC) curves and Youden's J index to establish putative thresholds to dichotomize percent change for each CloFAL parameter. If this approach was non-informative, we planned to use a threshold of 50% change (specifically, ≥50% increase for MA and AUC0-60 min, and a ≥50% decrease for T1 and FI2), conservatively selected to assure that this threshold was substantively greater than the inter-assay coefficient of variation of the assay for each parameter.

Associations with VTE recurrence for the aforementioned dichotomized variables for marked subacute changes in CloFAL parameters and for elevated D-dimer levels at 3 months were determined by univariable logistic regression with Firth's penalized likelihood approach, to obtain odds ratios (OR) and 95% confidence intervals (CIs). For this aim, patients in whom VTE recurrence occurred before 3 months post-diagnosis of the index VTE (n=1) were excluded from the analysis. Sensitivity was also calculated from the proportion of patients with recurrent VTE in which the prognostic laboratory variable of interest was positive. Specificity was defined as the proportion of patients without recurrent VTE in which the laboratory determinant was negative.

Positive likelihood ratios were calculated as sensitivity÷(1-specificity). Change in pre-test to post-test probability of recurrent VTE was calculated using the positive likelihood ratio, as previously described (Goldenberg N A, Knapp-Clevenger R, Manco-Johnson M J, et al. Mountain States Regional Thrombophilia Group. Elevated plasma factor VIII and D-dimer levels as predictors of poor outcomes of thrombosis in children. N Engl J Med. 2004; 351(11):1081-8). All statistical analyses were performed using SAS v 9.4 and Stata v 15, with statistical significance defined as a two-sided alpha ≤0.05.

Descriptive statistics were used to summarize data on patient characteristics, VTE presentation, treatment, and outcomes. To explore prognostic cutoffs for percent change in each parameter receiver operating characteristics curves were generated, and inter-assay coefficients of variation of the assay were also considered. Thresholds of 50% increase in MA or $AUC_{60}$, or 50% decrease in T1, were ultimately selected as candidate phenotypes of relative rebound hypercoagulability. An association between marked rise in plasma coagulability during the subacute period post-VTE and VTE recurrence was determined via univariate logistic regression, using odds ratios (OR) and 95% confidence intervals (CI), with two-sided alpha=0.05. The blind was maintained in the Kids-DOTT trial throughout data transfer and analysis.

Results: The final study population consisted of 88 patients, with a median age of 12.6 years (range, 0.01-20.8 years). VTE was classified as provoked in 98% of cases. Patient and VTE characteristics at baseline and outcomes during follow-up are shown in Table 1. Median follow up time was 52 weeks (range 9-123 weeks). A marked rise in plasma coagulability during the subacute period post-diagnosis of VTE was found in 13% of the study population. Recurrent VTE developed in 10% of patients. Logistic regression analysis revealed that change in CloFAL $AUC_{60}$ and T1 were not prognostic of VTE recurrence. However, a marked rise in plasma coagulability during the subacute period post-diagnosis of VTE, as measured by change in CloFAL MA, was associated with a statistically significant, 4-fold increase in the risk of recurrent VTE (OR=4.47, 95% CI=1.05-19.0; P=0.04).

TABLE 1

Patient and VTE characteristics at baseline and outcomes during follow-up.

| | Patients (n= 88) |
|---|---|
| Median age (range) | 12.6 (0.01-20.8) |
| Gender female no. (%) | 49 (55.6) |
| Location Index VTE no. (%) | |
| Upper Extremity | 28 (31.8) |
| Lower Extermity | 37 (42.0) |
| CSVT | 12 (13.6) |
| Other* | 11 (12.5) |
| Type of VTE no. (%) | |
| Provoked | 87 (98.8) |
| Unprovoked | 1 (1.2) |
| CVC-associated VTE no. (%) | 48 (54.5) |

TABLE 1-continued

Patient and VTE characteristics at baseline and outcomes during follow-up.

|  | Patients (n= 88) |
| --- | --- |
| Recurrent VTE no. (%) | 9 (10.2) |
| Marked subacute rise in coagulability** no. (%) | 12 (13.6) |
| Median Follow up weeks (range) | 52 (9-123) |

Abbreviations: VTE: venous thromboembolism; CSVT: cerebral sinovenous thrombosis; CVC: central venous catheter.
*Other: included internal jugular vein only, superior vena cava only, and splanchnic vein only.
**As defined by the number of patients exhibiting a 50% or greater increase in MA in the CloFAL assay at 3 months relative to 4-6 weeks post-diagnosis of VTE FIG. 1 provides ROC curves for subacute change (measurements at 3 months vs. 4-6 weeks post-diagnosis of index VTE) in each CloFAL assay parameter of interest. C-indices were as follows: AUC, 0.65; MA, 0.71; T1, 0.66; FI2, 0.44. Using Youden's J index, the following prognostic thresholds for subacute change in CloFAL parameters were initially determined: increase in AUC, 10.3%; increase in MA, 10.0%; decrease in T1, 1.4%; decrease in $FI_2$ 1.1%. Because each of these derived thresholds fell within the corresponding inter-assay coefficient of variation for CloFAL assay parameters, the secondary approach of prognostic threshold evaluation was employed, in which a marked subacute rise in coagulability was set at a 50% change in MA, AUC, or T1, and a marked subacute decline in fibrinolytic capacity was set at a 50% change in $FI_2$.

Figure 2:
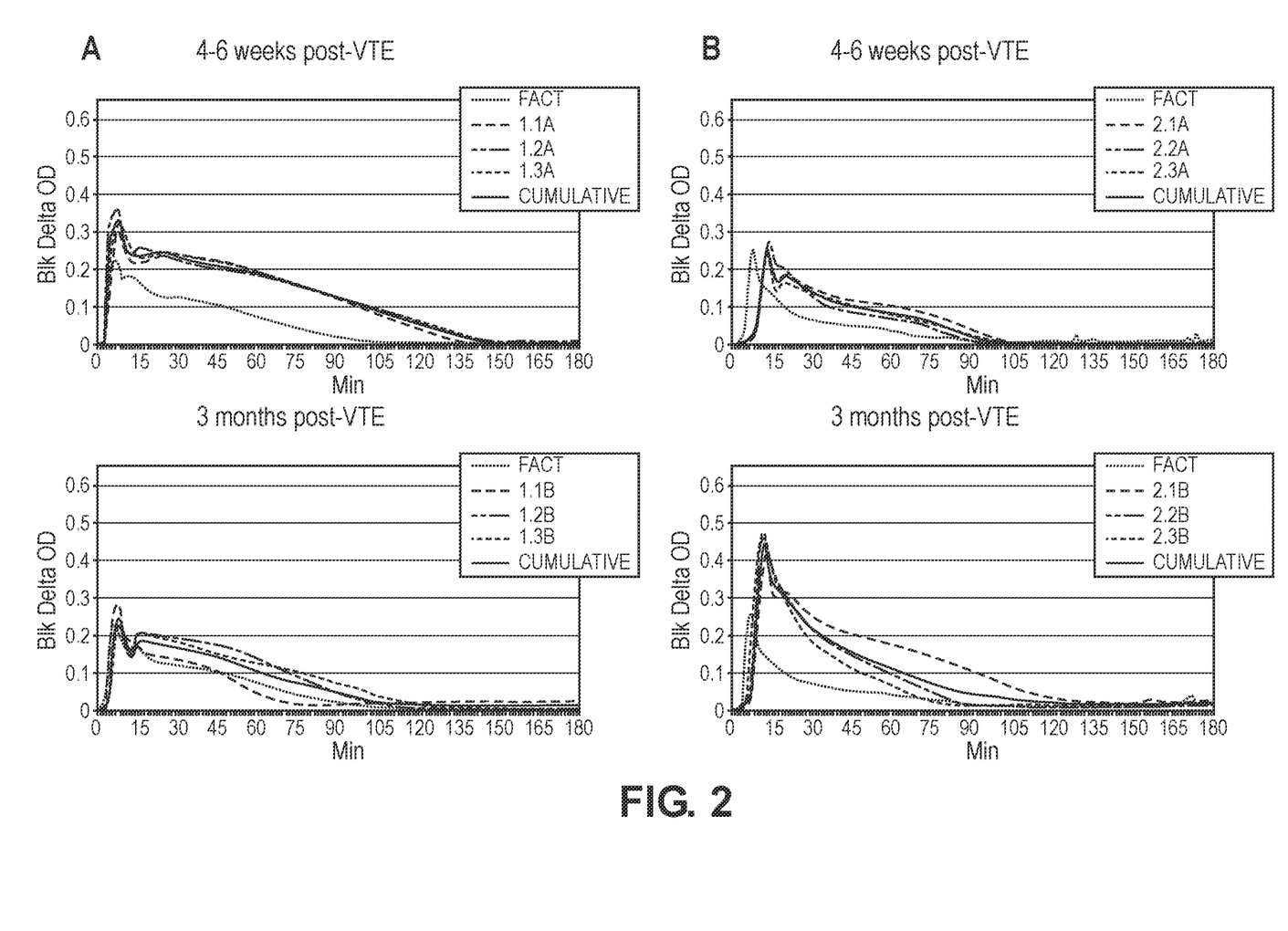

Table 2 shows the distribution of CloFAL parameters and their association with recurrent VTE. D-dimer was elevated at 3 months in 18 patients (20.9%). By comparison, a marked subacute rise in coagulability (see Methods) was observed in 15 patients (17.4%) by CloFAL MA, in 14 patients (16.2%) by $AUC_{0\text{-}60}$ min, and in only one patient (1.1%) by T1. Two patients (2.3%) showed a marked subacute decline in fibrinolytic capacity, as measured by CloFAL $FI_2$. FIG. 2 shows representative CloFAL curves of patients with and without a marked subacute rise in coagulability by CloFAL MA and AUC. There was no significant association between elevated D-dimer levels at 3 months and subacute rise in coagulability as measured by ≥50% increase in MA or AUC (Fisher's exact P=0.29, and P>0.99, respectively).

Univariable logistic regression analyses (Table 2) revealed that a marked subacute rise in coagulability as defined by CloFAL MA was associated with a statistically-significant, six-fold increase (OR=5.87, 95% CI=1.34-25.8; P=0.019) in the odds of recurrent VTE. Neither the subacute change in CloFAL AUC, T1, or $FI_2$, nor an elevated D-dimer level at 3 months, was significantly associated with the risk of recurrent VTE. Similarly, neither a ≥50% increase in D-dimer levels at 3 months relative to 4-6 weeks post-VTE diagnosis, nor a change in D-dimer from negative at 4-6 weeks to positive at 3 months, were associated with an increased risk for recurrent VTE (Table 2).

A marked subacute rise in coagulability by CloFAL MA was observed in 22% of patients who were receiving anticoagulation, and in 13% of patients who were not receiving anticoagulation, at 3 months post-diagnosis of the index VTE. We determined a positive likelihood ratio of 4.73 (95% CI 1.33-16.8) for the association of a subacute rise in coagulability by CloFAL MA with the subsequent development of recurrent VTE. Given this likelihood ratio, and a pre-test probability of recurrent VTE of 10.3% (i.e., prevalence in the study population), the post-test probability of recurrent VTE in the setting of provoked VTE with a subacute rise in coagulability by CloFAL MA was 35.2%.

TABLE 2

Marked rise in coagulability in the subacute period post-diagnosis of VTE, D-dimer and risk of recurrent VTE

| Putative Prognostic Factor* | Frequency in Study Population n (%) | OR | Measure of Association with Recurrent VTE 95% CI | P-value |
| --- | --- | --- | --- | --- |
| CloFAL MA | 15 (17.2) | 5.87 | 1.34-25.8 | 0.019 |
| CloFAL $_{AUC0\text{-}60\ min}$ | 14 (16.1) | 3.74 | 0.82-17.0 | 0.089 |
| CloFAL T1 | 1 (1.1) | 3.01 | 0.03-297.3 | 0.638 |
| CloFAL $FI_2$ | 2 (2.3) | 1.8 | 0.04-79.4 | 0.761 |
| Elevated D-dimer at 3 mos. | 10 (20.7) | 1.46 | 0.30-7.15 | 0.643 |

Abbreviations: VTE, venous thromboembolism; CI, confidence interval; MA, maximum amplitude; AUC, area under the curve; Tl, time to maximum amplitude; $FI_2$, modified fibrinolytic index.
*CloFAL parameters were evaluated for subacute change (3 month vs. 4-6 week measurements).
†Elevated D-dimer was defined as >0.42 µgFEU/mL Conclusions: A marked rise in plasma coagulability during the subacute period post-diagnosis of VTE, as measured by change in MA in the CloFAL assay, developed in 13% of a multicenter study population of patients <21 years of age with predominantly-provoked VTE, and was associated with a 4-fold increased risk of recurrent VTE. Future work will seek to investigate mechanisms underlying the rise in plasma coagulability during the subacute phase post-diagnosis of VTE in young patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for identification or diagnosis and treatment of a subject who is at risk for recurrent thromboembolism and who previously experienced a thrombotic event (TE) and underwent coagulation therapy comprising the steps of: a) analyzing a first biological sample taken from the subject at a time period of about 6 weeks +/- 2 weeks prior to planned cessation of coagulation therapy using the CloFAL method and generating a CloFAL maximum amplitude value; b) analyzing a second biological sample taken from the subject at time of planned cessation (or within about 2 weeks post-cessation) of anticoagulation therapy using the CloFAL method and generating a CloFAL maximum amplitude value; c) comparing the CloFAL maximum amplitude value of a) to b); identifying the subject as being at heighted risk for recurrent thromboembolism based on the CloFAL maximum amplitude value of b) being at least 50% greater than the CloFAL maximum amplitude value of a); and e) administering to the subject identified as at risk for a recurrent TE an antithrombic therapeutic regimen.

2. The method of claim 1, wherein the second biological sample is taken from the subject at time period of about at least one 1 month to about 24 months post-cessation of coagulation therapy.

3. The method of claim 2, wherein the second biological sample is taken from the subject at time period at least about 3 months post-cessation of coagulation therapy.

4. The method of claim 1, wherein the biological sample is a blood sample.

5. The method of claim 1, wherein the biological sample is a plasma sample.

6. The method of claim 1, wherein the TE is provoked.

7. The method of claim 1, wherein the TE is unprovoked.

8. A method for diagnosing and treating a risk of a recurrent thrombotic event (TE) in a subject who previously experienced a TE and has undergone anticoagulation therapy, comprising the steps of:
   a) analyzing a first biological sample taken from the subject at a time period of about 4 to about 6 weeks post-diagnosis of TE, using the CloFAL assay method and generating a CloFAL MA value;
   b) analyzing a second biological sample taken from the subject at a time period of at least about 3 months post-diagnosis of TE using the CloFAL assay method and generating a CloFAL MA value;
   c) comparing the CloFAL maximum amplitude value of a) to b); and
   d) identifying the subject as being at risk for a recurrent TE based on the CloFAL MA value of b) being at least 50% greater than the CloFAL MA value of a); and
   e) administering to the subject identified as at risk for a recurrent TE an antithrombic therapeutic regimen.

9. The method of claim 8, wherein the second biological sample is taken from the subject at a time period of about 6 months post-diagnosis of TE.

10. The method of claim 8, wherein the second biological sample is taken from the subject at a time period of greater than 6 months post-diagnosis of TE.

11. The method of claim 8, wherein the biological sample is a blood sample.

12. The method of claim 8, wherein the TE was a provoked TE.

* * * * *

UNITED STATES PATENT AND TRADEMARK OFFICE
CERTIFICATE OF CORRECTION

PATENT NO. : 11,789,030 B2
APPLICATION NO. : 17/398695
DATED : October 17, 2023
INVENTOR(S) : Neil Goldenberg Page 1 of 1

It is certified that error appears in the above-identified patent and that said Letters Patent is hereby corrected as shown below:

In the Claims

In Claim 1, Column 19, Line 22, "value of a) to b); identifying the subject as being at heighted" should read --value of a) to b); d) identifying the subject as being at heighted--; and In Claim 8, Column 20, Line 18, "to b); and" should read --to b);--.

Signed and Sealed this
Fifth Day of December, 2023

Katherine Kelly Vidal
*Director of the United States Patent and Trademark Office*